(12) United States Patent
Leigh

(10) Patent No.: US 11,234,934 B1
(45) Date of Patent: Feb. 1, 2022

(54) DRUG AND SMALL MOLECULE DELIVERY VIA MICROBIAL VESICLES

(71) Applicant: Sunny Leigh, Issaquah, WA (US)

(72) Inventor: Sunny Leigh, Issaquah, WA (US)

( * ) Notice: Subject to any disclaimer, the term of this patent is extended or adjusted under 35 U.S.C. 154(b) by 0 days.

(21) Appl. No.: 16/112,459

(22) Filed: Aug. 24, 2018

Related U.S. Application Data

(60) Provisional application No. 62/549,475, filed on Aug. 24, 2017, provisional application No. 62/549,487, filed on Aug. 24, 2017.

(51) Int. Cl.
*A61K 9/127* (2006.01)
*A61K 47/46* (2006.01)

(52) U.S. Cl.
CPC ............ *A61K 9/1277* (2013.01); *A61K 47/46* (2013.01)

(58) Field of Classification Search
None
See application file for complete search history.

(56) References Cited

U.S. PATENT DOCUMENTS 9,351,931 B2    5/2016   Huang

OTHER PUBLICATIONS

Wessel et al J Bacteriol. Jan. 2013; 195(2):213-9 (Year: 2013).*
Zhao, et al Infect Immun. Dec. 2013; 81(12): 4509-4518 (Year: 2013).*
Macdonld et al ,Bacteriol. Jul. 2013; 195(13):2971-81 (Year: 2013).*
Mogna et al 2012J.Clin, Gasteroenterol; vol. 46, S41-45. (Year: 2012).*
Perricone et al Beverages 2015, 1, 95-103 (Year: 2015).*
Li et al 2017; BMC Microbiology 17:66 (Year: 2017).*
Image from The Nobel Prize in Physiology or Medicine 2013, The Nobel Committee for Physiology or Medicine, 1 page.
Zierath, J, et al., "Machinery Regulating Vesicle Traffic, A Major Transport System in our Cells," The Nobel Assembly at Karolinska Institutet, 6 pages.
Koppel, N et al, "Chemical transformation of xenobiotics by the human gut microbiota," Science, Jun. 23, 2017, 13 pages.
Delzenne, M et al., "Contribution of gut microbiota—host cooperation to drug efficacy" Nature Reviews Gastroenterology & Hepatology, available on-line Dec. 20, 2017, 3 pages.
J, Christian "Precision medicine using microbiota," Science, Jan. 5, 2018, 4 pages.
Van Niel, G et al., "Shedding light on the cell biology of extracellular vesicles," Nature Reviews Molecular Cell Biology, Jan. 17, 2018, 16 pages.
Carmody, R et al., "Host-microbial interactions in the metabolism of therapeutic and diet-derived xenobiotics," The Journal of Clinical Investigation, Aug. 8, 2014, 21 pages.
Reyes, L et al., "Improving carotenoids production in yeast via adaptive laboratory evolution," Journal of Metabolic Engineering, Nov. 18, 2013, 8 pages.
Yang, Yu et al., "Biodegradation and Mineralization of Polystyrene by Plastic-Eating Mealworms: Part 2. Role of Gut Microorganisms" Journal of Environmental Science and Technology, Sep. 21, 2015, 7 pages.
Iida, N et al., "Commensal Bacteria Control Cancer Response to Therapy by Modulating the Tumor Microenvironment," Science, Nov. 22, 2013, 5 pages.
Viaud, S et al., "The intestinal microbiota modulates the anticancer immune effects of cyclophosphamide," Science, Nov. 22, 2013, 15 pages.
Daillere, R et al., "Enterococcus hirae and Barnesiella intestinihominis Facilitate Cyclophosphamide-Induced Therapeutic Immunomodulatory Effects," Immunity, Oct. 18, 2016, 45 pages.
Vetizou, M et al., "Anticancer immunotherapy by CTLA-4 blockade relies on the guy microbiota," Science, Nov. 27, 2015, 7 pages.
Sivan, A et al., "Commensal Bifidobacterium promotes antitumor immunity and facilitates anti-PD-L1 efficacy," Science, Nov. 5, 2015, 7 pages.
Routy, B et al., "Gut microbiome influences efficacy of PD-1-based immunotherapy against epithelial tumors," Science, Nov. 2, 2017, 72 pages.
Gopalakrishnan, V et al., "Gut microbiome modulates response to anti-PD-1 immunotherapy in melanoma patients," Science, Jan. 5, 2018, 105 pages.
Geller, L et al., "Potential role of intratumor bacteria in mediating tumor resistance to the chemotheraputic drug gemcitabine," Science, Sep. 15, 2017, 6 pages.
Bullman, S et al., "Analysis of Fusobacterium persistence and antibiotic response in colorectal cancer," Science, Dec. 15, 2017, 11 pages.
Maier, L et al., "Extensive impact of non-antibiotic drugs on human gut bacteria," Nature, Mar. 29, 2018, 26 pages.
Matsumura, Y et al., "A New Concept for Macromoleculat Therapeutics in Cancer Chemotherapy: Mechanism of Tumoritropic Accumulation of Proteins and the Antitumor Agent Smancs," Cancer Research, Dec. 1986, 7 pages.
Mogna, L et al., "Selenium and zinc internalized by Lactobacillus buchneri Lb26 (DSM 16341) and Bifidobacterium lactis Bb1 (DSM 17850): improved bioavailability using a new biological approach," Journal of Clinical Gastroenterology, Oct. 2012, 6 pages.
Westfall, P et al., "Production of amorphadiene in yeast, and its conversion to dihydroartemisinic acid, precursor to the antimalarial agent artemisinin," Proceedings of the National Academy of Sciences, Jan. 12, 2017, 9 pages.

(Continued)

*Primary Examiner* — Padmavathi Baskar
(74) *Attorney, Agent, or Firm* — Alleman Hall Creasman & Tuttle LLP

(57) ABSTRACT

A method comprises preparing initial agent molecules and applying the initial agent molecules to microbes for extracellular vesiculation. Microbial vesicles are generated which contain the initial agent molecules by the microbes. The packaged microbial vesicles are then administered to a host organism. By administering the initial agent molecules as a microbial vesicle package, binding proteins for the initial agent molecules may be co-administered, and cells may uptake numerous initial agent molecules concurrently.

7 Claims, 9 Drawing Sheets

(56) References Cited

OTHER PUBLICATIONS

Bober, J et al., "Synthetic Biology Approaches to Engineer Propeiotics and Members of the Human Microbiota for Biomedical Applications," The Annual Review of Biomedical Engineering, Jun. 4, 2018, 24 pages.

Hove, H et al., "Lactic acid bacteria and the human gastrointestinal tract," European Journal of Clinical Nutrition, May 1999, 12 pages.

Lefrancais, E et al., "The lung is a site of platelet biogenesis and a reservoir for haematopoietic progenitors," Nature, Apr. 6, 2017, 18 pages.

Brown, L et al., "Through the wall: extracellular vesicles in Gram-positive bacteria, mycobacteria and fungi," Nature Reviews. Microbiology., Oct. 13, 2015, 29 pages.

Soares, R et al., "Highlists of the Sao Paulo ISEV workshop on extracellular vesicles in cross-kingdom communication," Journal of Extracellular Vesicles, Nov. 26, 2017, 13 pages.

Vicariotto, F et al., "Effectiveness of the association of 2 probiotic strains formulated in a slow release vaginal product, in women affected by vulvovaginal candidiasis: a pilot study," Journal of clinical gastroenterology, Oct. 2012, 8 pages.

Matuskova, Z et al., "Administration of a Probiotic Can Change Drug Pharmacokinetics: Effect of *E. coli* Nissle 1917 on Amidarone Absorption in Rats," PLOS One, Feb. 5, 2014, 5 pages.

Wang, W et al., "Exposure to concentrated ambient PM2.5 alters the composition of guy microbiota in a murine model," Particle and Fibre Toxicology, Dec. 2018, 13 pages.

Want, K et al., "Structural Modification of Natural Product Ganomycin I Leading to Discovery of a $\alpha$-Glucosidase and HMG-CoA Reductase Dual Inhibitor Improving Obesity and Metabolic Dysfunction in Vivo," Journal of Medicinal Chemistry, Apr. 10, 2018, 17 pages.

Galaniei, S et al., "Complete biosynthesis of opoids in yeast," Science, Aug. 6, 2015, 7 pages.

Gaulke, C et al., "Triclosan Exposure Is Associated with Rapid Restructuring of the Microbiome in Adult Zebrafish," PLOS One, May 18, 2016, 20 pages.

Mor, G et al., "Trophoblast-microbiome interaction: a new paradigm on immune regulation," American Journal of Obstetrics and Gynecology, Oct. 2015, 7 pages.

\* cited by examiner

```
                        200
                           ↘

┌─────────────────┐ ─ 210
                    │ PREPARE INTIAL  │
                    │ AGENT MOLECULES │
                    └─────────────────┘
                             │
                             ▼
                    ┌─────────────────┐ ─ 220
                    │ APPLY INITIAL   │
                    │ AGENT MOLECULES │
                    │ TO MICROBES FOR │
                    │ E-VESICULATION  │
                    └─────────────────┘
                             │
                             ▼
              ┌─────────────────────┐ ─ 230         ┌─────────────────────┐ ─ 270
              │ GENERATE MICROBIAL  │               │ PREPARE MICROBES AND│
              │ VESICLES CONTAINING │──────────────▶│ VESICLES FOR STORAGE│
              │ INITIAL AGENT       │               │ AND PACKAGING       │
              │ MOLECULES           │               └─────────────────────┘
              └─────────────────────┘                         │
                         │                                    ▼
                         ▼                         ┌─────────────────────┐ ─ 280
              ┌─────────────────┐ ─ 240            │ ADMINISTER PACKAGED │
              │ ISOLATE VESICLES│                  │ MICROBES AND VESICLES│
              │ FROM MICROBES   │                  └─────────────────────┘
              └─────────────────┘
                         │
                         ▼
              ┌─────────────────────┐ ─ 250
              │ PREPARE ISOLATED    │
              │ VESICLES FOR STORAGE│
              │ AND PACKAGING       │
              └─────────────────────┘
                         │
                         ▼
              ┌─────────────────┐ ─ 260
              │ ADMINISTER      │
              │ PACKAGED        │
              │ VESICLES        │
              └─────────────────┘
```

FIG. 2

DRUG AND SMALL MOLECULE DELIVERY VIA MICROBIAL VESICLES

CROSS REFERENCE TO RELATED APPLICATIONS

This non-provisional application claims priority to U.S. provisional patent application Ser. No. 62/549,475, filed Aug. 24, 2017, titled "GROW PROBIOTICS IN PRESENCE OF CHEMICALLY SYNTHESIZED DRUGS TO CONVERT THESE CHEMICAL DRUGS INTO THEIR BIO-ACTIVE FORMS AND ADMINISTER THESE BIO-ACTIVE FORMS INSTEAD OF THEIR CHEMICAL FORMS FOR BETTER ABSORPTION AND UPTAKE," and also claims priority to U.S. provisional patent application Ser. No. 62/549,487, filed Aug. 24, 2017, titled "GROW ENDOPHYTE BACTERIA IN PRESENCE OF SYNTHESIZED FERTILIZERS OR PESTICIDES TO CONVERT THESE SYNTHESIZED FERTILIZERS OR PESTICIDES INTO THEIR BIO-ACTIVE FORMS AND ADMINISTER THESE BIO-ACTIVE FORMS INSTEAD OF THEIR CHEMICAL FORMS FOR BETTER ABSORPTION AND UPTAKE," the entire contents of each of which is incorporated herein by reference for all purposes.

BACKGROUND

Commercial therapeutic or nutraceutical agents for humans, animals, and plants are either derived through synthesis, semi-synthesis, or purification from a natural source. The derived agents are packaged as purified compounds which may have low bioavailability, or as complexes with arbitrarily selected proteins. This may increase consumer drug costs, as only a portion of the ingested dosage is taken up by the host organism. Additionally, such agents may generate side effects and/or toxicity in the host, and may hasten the host's resistance to the agent.

SUMMARY

According to an aspect of the present disclosure, an example method comprises preparing initial agent molecules and applying the initial agent molecules to microbes for extracellular vesiculation. Microbial vesicles are generated which contain the initial agent molecules by the microbes. The packaged microbial vesicles are then administered to a host organism. By administering the initial agent molecules as a microbial vesicle package, binding proteins for the initial agent molecules may be co-administered, and cells may uptake numerous initial agent molecules concurrently.

BRIEF DESCRIPTION OF THE DRAWINGS

FIG. 2 depicts a flow-chart for a method of preparing and administering agent molecules via microbial vesicles.

DETAILED DESCRIPTION

Figure 1:
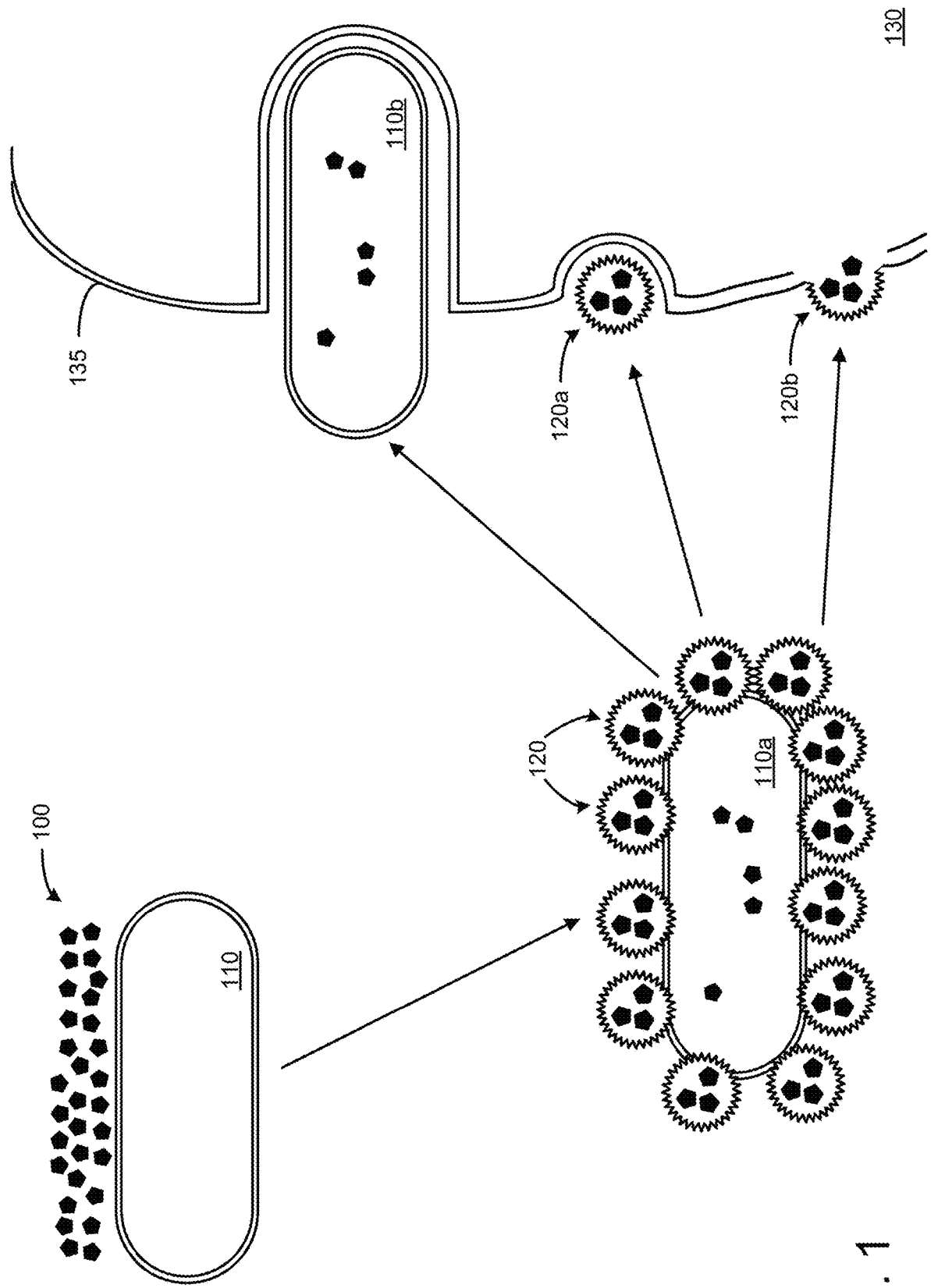
FIG. 1 illustrates the application of exogenous molecules to a microbe, the generation of vesicles containing exogenous molecules by the microbe, and the uptake of microbes and vesicles by a mammalian cell.

Commercial drug development often involves the synthesis and screening of numerous compounds. While these compounds may be effective once they have engaged a cell, most do not have specific cellular chaperones, and are typically taken in a purified form, without chaperones that may direct the compounds to the desired location. As such, the compounds must be presented in exceedingly high quantities to generate a response. This both increases the cost of the compounds and increases the risk of deleterious effects of metabolites.

For plant-based therapeutics, it is the inventor's understanding that research has demonstrated that patients often respond better to unrefined extracts when compared to purified or synthesized compounds (see e.g., "Structural Modification of Natural Product Ganomycin I Leading to Discovery of a α-Glucosidase and HMG-CoA Reductase Dual Inhibitor Improving Obesity and Metabolic Dysfunction in Vivo" by Wane et al., published in the Journal of Medicinal Chemistry on Apr. 26, 2018). One potential reason for this discrepancy may be that the purified chemicals have diminished uptake by cells when compared with impure extracts that include other lysates from the source organism. Such lysates may include proteins which bind to the chemicals, stabilizing the chemicals and/or facilitating cellular uptake. The lysates may also include membrane fragments which may, under some conditions, form micelles and/or vesicles which may encapsulate the chemicals. Such biochemical packages may increase rates of uptake by providing a concentrated volume of chemicals which may be internalized by a cell. The packaging may further prevent degradation of the contents, thus potentially increasing the efficacy of the chemicals.

Indeed, it has been shown that minerals such as selenium and zinc are both absorbed much better and more capable of reaching target membranes in mammalian cells when first vesiculated/internalized by bacteria. Concomitant administration of probiotic bacteria in mice and rats been shown to increase uptake and delivery of small molecules, minerals, and peptides. Indeed, organisms that are microbiota depleted (e.g., germ-free or antibiotics-treated) have been shown to have reduced uptake and processing of exogenous molecules and are less responsive to anti-tumor agents than are organisms having full microflora complements. These phenomena are not limited to mammalian systems, as worms, zebrafish and plants also are known to rely on resident microbiota to facilitate uptake of exogenous molecules. It has been demonstrated that exogenous molecules, such as marketed drugs, pure extracts from a natural source, PM2.5, etc., inhibit the function of the host's microbiota. The conventional administration of a marketed drug does not allow enough time for the drug to persist within the host to be fully extracellularly-vesiculated by the host microbiota. Additionally, the drug may be hijacked by "bad" bacteria, thus resulting in overdosage, unwanted side effects or drug resistance. Therefore, fully vesiculating agent molecules in vitro prior to administration would effectively and significantly reduce drug dosage, improve drug efficacy, permanently eliminate drug toxicity, side effect, resistance, or excrement contamination to the environment.

FIG. 1 illustrates the extracellular vesiculation (E-vesiculation) of agent molecules 100 by a microbe 110, the generation of vesicles 120 containing the agent molecules 100, and the uptake of microbe 110 and vesicles 120 by a mammalian cell 130.

Both prokaryotic and eukaryotic microbes secrete proteins, molecules, polysaccharides and other factors via vesicles 120. For example, gram-positive bacteria may generate extracellular membrane vesicles (EVs), gram-negative bacteria may generate outer membrane vesicles (OMVs), while eukaryotic cells, such as yeast and other fungi may generate intracellular vesicles (IVs). Such vesicles consist of lipid-bilayers that form lumen-containing spheres typically ranging in size from 20 nm to 500 nm in diameter.

E-vesiculation may be considered a natural process during which prokaryotes directly shed membranes to form microbiota-derived extracellular vesicles (MDEVs) (e.g., OMVs or EVs) to vesiculate (internalize/process) exogenous molecules existing outside around their membranes into vesicles 120. These vesicles 120 may be shed directly from their cell membranes to the extracellular environment. The inventor believes that both in vivo and in vitro, prokaryotes uptake exogenous molecule outside their cells differently from eukaryotes. What prokaryotes uptake into their cells are the necessary nutrients only; everything else other than those necessary nutrients are directly wrapped into MDEVs shed from their cell membranes.

MDEVs are the major transport system for transport and uptake of xenobiotics in a eukaryotic host, as most host eukaryotic cells are not able to extracellularly vesiculate xenobiotics as its resident prokaryotes do. Rather, the host relies on its resident prokaryotes to E-vesiculate first and then transport exogenous molecules via these MDEVs to target cells for uptake. Like their counterpart intracellular vesicles produced by eukaryotic cells, these MDEVs also have proteins on their membranes and carry hereditary information.

Resident bacteria E-vesiculate exogenous chemical molecules by internalizing them into MDEVs they produce with binding proteins, thus bio-transforming purified exogenous chemical molecules into bio-active holistic vesicle complexes. Proteins on the MDEVs' membrane enable the whole vesicle complex to deliver, fuse and release the once exogenous cargo molecules at the right host locations.

The MDEVs may E-vesiculate and transport exogenous molecules such as nutraceutical or therapeutic agents derived through synthesis, semi-synthesis, or purification from a natural source for uptake. This allows the host to actively, effectively and efficiently control uptake of xenobiotics and nutrients, and at the same time to prevent free invasion from xenobiotics.

Under some conditions, the outer membranes of bacteria act as a molecular sieve, allowing for non-specific uptake of molecules within their growth media. In particular, gram-positive bacteria, (e.g., *Lactococcus lactis*), having only a single membrane, are capable of being loaded with both small molecules and large peptides. Gram-negative bacteria. (e.g., *Escherichia coli*) rely on outer-membrane channels to facilitate movement of molecules into the cell, and thus tend to be limited to uptake of small molecules and peptides. Affording this size restriction, if agent molecules 100 are placed in microbial growth media, microbes 110 will uptake some agent molecules 100 in a concentration dependent manner, as shown at 110*a*. Under some conditions, the vesicles 120 may carry cargo derived from the contents of the parent microbe 110*a*.

Mammalian cells 130 may uptake microbes 110 and vesicles 120 in numerous ways. Professional phagocytes, such as macrophages and dendritic cells, may engulf entire microbes 110*b* through the process of phagocytosis. The microbe binds receptors on the cell membrane 135, which in turn invaginates to engulf the microbe, generating a phagosome. The microbe is then digested through the fusion of lysosomes to the phagosome. Desired contents may be repackaged within the cell, and undesired waste products may be released via an exosome. In some examples, microbes 110*b* including vesicles 120 may be phagocytosed as a collective unit.

Smaller particles, such as vesicles 120*a* may be uptaken via phagocytosis or receptor-mediated endocytosis. This process is similar to phagocytosis, but relies on highly specific membrane receptors, and the generation of a coated internal vesicle. The particle is dissociated from the receptor and degraded, with small molecules sorted for degradation or repackaging.

In some examples, vesicles 120*b* may fuse directly with the cell membrane 135. By directly fusing to cell membrane 135, contents of vesicles 120*b* are released into the cytoplasm of mammalian cell 130, and not directly shunted into a digestive pathway. Such membrane fusion is dependent on the presence of lipid rafts as well as specific receptors on cell membrane 135. This mechanism is often co-opted by pathogenic bacteria, but may be utilized by microbes to regulate host immunity for their benefit. One or more of these delivery mechanisms may be exploited to generate a method for delivery of drugs or other molecular agents whereby the agent molecules are packaged by microbes into vesicles which are then administered to patients. FIG. 2 depicts a flow chart for a method 200 for preparing and administering agent molecules via microbial vesicles. Method 200 may be applied as a whole or in part to prepare and/or administer agent molecules to a host organism via microbial vesicles. Method 200 may be applied to all marketed drugs, both currently available or later developed, including biologics, for human and animals.

At 210, method 200 includes preparing initial agent molecules. Initial agent molecules may be prepared via extraction or partial extraction from a natural production source, via synthesis, via semi-synthesis, etc. In some examples, the initial agent molecules may include precursors for an active form of the agent molecules. The initial agent molecules may undergo enzymatic modification and/or metabolism to generate the active agent molecules.

In some examples, the initial agent molecules may include one or more additional moieties that are not included in the active agent molecules. Such moieties may promote uptake of the initial agent molecules by the microbes, may protect the agent molecules from degradation and/or metabolism, may promote binding of the initial agent molecules to one or more proteins, may promote solubility of the initial agent molecules, etc. Such moieties may be naturally occurring and/or added during synthesis or semi-synthesis of the initial agent molecules.

Such additional moieties may be designed to be removed at one or more specific locations, such as within the microbes following uptake of the initial agent molecules, within generated microbial vesicles, following delivery into the human subject (e.g., in the gastrointestinal (GI) tract, by endogenous microbes residing in the GI tract, within the target cells). The additional moieties may thus promote stability of the agent molecules, trafficking of the agent molecules, targeting of the agent molecules, etc.

Initial agent molecules may include chemical exogenous molecules such as nutraceutical or therapeutic agent derived through synthesis, semi-synthesis, or purification from a natural source or anything derived from the environment. In some examples, the initial agent molecules may include man-made exogenous protein molecules such as biologics, for example, anti-PD-1/PD-L 1 antibodies.

At 220, method 200 includes applying the initial agent molecules to microbes for E-vesiculation. Microbes may include gram-positive probiotic bacteria such as, but not limited to, *Bifidobacterium longum, Bifidobacterium lactis, Bifidobacterium animalis, Bifidobacterium breve, Bifidobacterium infantis, Bifidobacterium adolescentis, Lactobacillus acidophilus, Lactobacillus casei, Lactobacillus paracasei, Lactobacillus salivarius, Lactobacillus reuteri, Lactobacillus rhamnoses, Lactobacillus johnsonii, Lactobacillus plantarum, Lactobacillus ferment, Lactococcus lactis, Streptococcus thermophiles, Streptomycis avermectis, Lactococcus lactis, Lactococcus diacetylactis, Lactococcus cremoris, Lactobacillus bulgaricus, Lactobacillus helveticus, Lactobacillus delbrueckii*, and mixtures thereof (e.g., VSL #3). In some examples, microbes may include gram-negative probiotic bacteria such as, but not limited to, *Escherichia coli*, Nissle 1917. In some examples, microbes may include probiotic yeast and/or other single-cell fungi, such as, but not limited to, *Saccharomyces boulardii*. Other, non-probiotic, microbes may also be used. For plants, microbes may include, but are not limited to soil bacteria such as *Bacillus subtilis, Pseudomonas fluorescens, Actinomycetes, Clostridium*, as well as other plant microbiota such as *Rhizobium* bacteria, soil fungi, soil algae, etc.

Microbes may be tested prior to application of the initial agent molecules to determine if they are safe for the prospective host organism. In particular, the microbes may be analyzed for any potential harmful activity with regard to the underlying reason for treatment (e.g., diabetes, immunocompromization, cancer, etc.).

Microbes may be grown in any suitable culture medium. Initial agent molecules may be applied to the microbes for E-vesiculation in the original growth medium, or in a medium specific for promoting E-vesiculation and/or microbial uptake. For example, the initial agent molecules may be applied in a growth medium that includes additional amino acids, peptides, sugars, etc. For initial agent molecules extracted from a natural production source, one or more components of the natural production source may be added to the growth medium. For example, the growth medium may be enriched with cold-pressed juices of the natural production source. In some examples, one or more reagents may be added to promote microbial tolerance of the initial agent molecules, to promote microbial uptake of the initial agent molecules, and/or to stabilize the initial agent molecules in the growth medium and/or within the microbes and/or vesicles following application.

Application may proceed for a predetermined duration and/or based on culture conditions. In some examples, the initial agent molecules may be replenished one or more times following the initial application. Uptake and/or E-vesiculation may be determined by assaying the media for depletion of the initial agent molecules, by assaying the microbes themselves (e.g., via spectrometry for color or fluorescence changes associated with uptake), or by any other suitable means.

At 230, method 200 includes generating microbial vesicles that contain the initial agent molecules. Upon application of the initial agent molecules, some microbes may generate vesicles that contain the initial agent molecules without additional stimulation. For example, gram-positive bacteria may generate extracellular membrane vesicles (EVs), gram-negative bacteria may generate outer membrane vesicles (OMVs), while eukaryotic cells, such as yeast and other fungi may generate intracellular vesicles (IVs). In some examples, one or more additional factors and/or molecules may be provided to the microbes in order to further stimulate vesicle formation. As an example, it has been shown that 2-heptyl-3-hydroxy-4-quinolone (PQS) stimulates MV formation in at least the gram-positive bacterium *P. aeruginosa*. As such, in some examples, one or more additional stimulatory molecules such as PQS may be added to the media containing the initial agent molecules. Such stimulatory molecules may be added concurrent with initial agent molecules, and/or may be added following incubation of the microbes with the initial agent molecules for a duration. Such a duration may be predetermined, or may be determined based on uptake of the initial agent molecules by the microbes.

In some examples, microbial vesicle formation may be induced by stress conditions. For example, the microbes may be subject to temperature changes (e.g., temperature increases), elevated temperatures, nutrient depletion, oxidative stress, and/or other compounds or conditions impacting membrane stability and/or integrity. Other factors have been shown to upregulate vesicle formation. For example, stress transcription factor sigma(B) upregulates production of MVs in *L. monocytogenes*. As such, stimulating factors such as sigma(B) may be applied via the culture media, via genetic upregulation, via induction of expression (e.g., in previously transformed microbes), etc. Similarly, repressive factors may be downregulated (e.g., via SiRNA) to induce vesicle formation.

Generating microbial vesicles may further include expressing and targeting proteins to the vesicles. For example, the microbes may be transformed to express proteins, either selectively or constitutively, that traffic to the vesicles upon vesicle generation. The microbes may be transformed with expression constructs that are inducible, responsive to one or more exogenously added molecules and/or to one or more endogenously generated proteins.

Proteins may be targeted to the vesicle lumen and/or periplasm, and may include proteins that function in signaling, stabilization, metabolism, etc. In some examples, membrane proteins that are endogenously expressed by the microbes may also be transgenically expressed in order to accommodate increased vesicle production. In some examples, membrane fusion proteins may be expressed, where an extra-vesicular portion of the membrane fusion protein includes a targeting sequence that may target the vesicle for uptake in specific cell types. In some examples, proteins may be expressed having one or more active sites that function within the vesicular periplasm. Such proteins may be membrane proteins or soluble proteins, and the active sites may function to bind, modify, metabolize, and/or otherwise interact with the initial agent molecules.

In some examples, membrane proteins may be expressed such that moieties for engaging a specific receptor are displayed on the external side of the vesicle. In some examples, the targeted receptor may be expressed on a particular cell type or types, and may be utilized to trigger and/or enhance internalization of the vesicle to a target cell. In some examples, multiple proteins may be expressed such that each vesicle is targeted to two or more cell types and/or receptor types. As an example, one or more types of cancer cell may be targeted by expressing proteins that bind to receptors expressed specifically on cancer cells, whereby the cancer cell would uptake the vesicle containing one or more anti-cancer drugs. Additionally or alternatively, a binding molecule may be generated which binds the cancer drug within the vesicle, but is only metabolizable within cancer cells. As such, if the vesicle were to be internalized by a normal cell, the cell would not be subject to the effects of the cancer drug. Only when internalized by a cancer cell, and when the binding molecule (e.g., a complementary synthetic vitamin) is subsequently metabolized, would the cancer drug be released and targeted for action.

In some examples, method 200 proceeds from 230 to 240. At 240, method 200 includes isolating vesicles from microbes. Following the generation of microbial vesicles loaded with initial agent molecules, the vesicles may be isolated from the microbes. However, depending on the microbes used, the vesicles may not be separated from the parent microbes. For eukaryotic microbes, such as yeast, the cell walls may first be broken down, as the vesicles are internally located. Cell wall breakdown may be performed via detergents, enzymes, hypotonic swelling, sonication, abrasives, pressure cells (e.g., French press), cell disruptors, other methods, and/or combinations of methods. Milder variations of such methods may also be applied to bacterial cultures to breakdown cell membranes and promote the release of vesicles from parent cells.

For bacteria and processed eukaryotic cells, intact microbes may be separated from large aggregates and vesicles, e.g., by low-speed centrifugation. In some examples, multiple centrifugation steps may be performed to sequentially remove cells, cell debris, and large protein and membrane aggregates. The culture media may additionally or alternatively be subject to sterile filtration to ensure removal of all intact microbes and particulate matter having a diameter greater than a threshold. Similarly, the culture media may be subject to ultrafiltration and/or precipitation in order to remove proteins with a molecular weight below a threshold. In some examples, microbial vesicles may be subject to affinity purification, e.g., by using a capture antibody, protein, or small molecule directed against a membrane protein known to be incorporated into the vesicles. Additionally or alternatively, microbial vesicles may be separated from intact microbes and smaller components via density gradient centrifugation and/or gel filtration. Separated vesicles may be further concentrated via precipitation, centrifugation, and/or other suitable methods.

At 250, method 200 includes preparing the isolated vesicles for storage and packaging. In particular, for vesicles isolated from gram-negative bacteria, lipopolysaccharides (LPS) and other toxins may be removed from membranes prior to packaging the vesicles for human administration. In some examples, this may be accomplished by pretreatment of the parent bacteria or isolated vesicles with detergents. Additionally or alternatively, the parent microbes may be genetically manipulated to produce a low-toxicity variant of LPS. Other toxins may be removed by genetic modification and/or by selecting low toxicity strains.

Isolated vesicles may be lyophilized (i.e., freeze-dried) and packaged for administration. Appropriate packaging of the isolated vesicles may be dependent on a selected mode of administration, as described at 260. Once lyophilized, the isolated vesicles may be packaged and/or stored for future use.

In some examples, the isolated vesicles may be packaged in a powder (i.e., dry) form. The lyophilized vesicles may be combined with one more additional dry components, for example, one or more additional sugars, proteins, small molecules, etc. The additional components may be selected to provide additional nutrients, co-factors, or therapeutics that may enhance or compliment the agents packaged within the vesicles. In some examples, the additional components may be selected to enhance delivery and/or solubility of the isolated vesicles. In some examples, the additional components may be selected to enhance uptake of the isolated vesicles by host cells and/or tissues. In some examples, the additional components may be provided to generate a suspension (e.g., beverage) to enable and/or enhance delivery of the isolated vesicles.

In some examples, the lyophilized vesicles may be resuspended in solution (e.g., aqueous solution), and may be co-suspended along with one or more additional components. Dry compositions and suspensions may be further packaged, for example by encapsulation. As an example, the vesicles may be packaged in a gelatin capsule. Additionally or alternatively, the vesicles may be packaged in an enteric capsule, enabling the capsule to remain intact through the stomach and allowing delivery of the vesicles to the small intestine for uptake.

However, an additional advantage of packaging exogenous agent molecules into MDEVs for oral ingestion is that the vesicles may have the additional benefit of being resilient in the harsh, acidic environment of the stomach. Based on the fact that *Lactobacillus* and *Bifidobateria* can survive in the presence of gastric acid, the inventor believes that probiotic-derived MDEVs would survive the gastric acid as well, as the MDEVs are much simpler in structure and smaller thus more morphologically stable than cells. However, if membranes of these MDEVs are damaged by food processing, cargo molecules inside these vesicles will be released as pure chemical molecules. Resident gut bacteria could repackage them in the same way that they process purified chemical drug molecules.

At 260, method 200 includes administering the packaged vesicles to a user. Depending on the packaging described at 250, the isolated vesicles may be administered to a user in numerous manners. The type of packaging and administration may be determined based on dosage, the target cells and/or tissues, etc. For example, the isolated vesicles may be administered orally, either as a powder, as a suspension, in encapsulated form, etc. Similarly, powders, suspensions, and capsules may be administered sublingually and/or buccally. Additionally or alternatively, encapsulated isolated vesicles may be administered rectally or vaginally. Suspensions of isolated vesicles may be administered ocularly, topically, transdermally, and/or parenterally (e.g., sub-cutaneously, intra-venously, intra-muscularly). Further, suspensions of isolated vesicles may be aerosolized and administered nasally or pulmonically. In some examples, the isolated vesicles may be utilized as the basis for adoptive cell transfer, whereby a subset of a patient's immune cells are isolated ex vivo, presented with the isolated vesicles for uptake, and then re-infused back to the patient.

For examples wherein the initial agent molecules have higher efficacy when packaged in microbial vesicles as compared to purified agent molecules, the intake dosage may be comparatively reduced. In some examples, the effects of the initial agent molecules may have an increased duration as compared to those of the purified agent, acting as a time-release agent, for example. As such, the frequency of dosing by the patient may be comparatively reduced.

Other manipulated chelated drug delivery systems do not survive the gastric acid. For example, in a chelated drug, the chelated amino acids would be broken down in the stomach and the once chelated chemicals would become pure chemicals again just as they were before chelation. Administration of exogenous drug molecules in their fully E-vesiculated form, together with the parent probiotics that produced the OMVs/EVs would significantly reduce drug dosage, improve drug uptake rate to 100% thus improve drug efficacy, eliminate drug side effect, toxicity, or drug resistance, and no drug will be excreted out of the body as it'd be 100% absorbed by the body, thus resulting no contamination to the environment. For drugs with known drug resistance, administration of their E-vesiculated form may make the drug effective again without concern about future drug resistance returning.

Additionally or alternatively, vesicles may be isolated from parent microbes prior to the application and uptake of the initial agent molecules. Microbial vesicles may be generated and isolated from parent microbes as described with regard to 230 and 240 of FIG. 2. The isolated microbial vesicles may then be loaded with the initial agent molecules by any suitable means, such as via electroporation. When the vesicle membranes have stabilized after a duration following electroporation, the loaded vesicles may be prepared for packaging, as described with regard to 250 of FIG. 2.

Alternatively, method 200 may proceed from 230 to 270. At 270, method 200 includes preparing microbes and vesicles for co-storage and co-packaging. In other words, microbial vesicles may be generated following application of the initial agent molecules, and then the microbes may be harvested and prepared for packaging without isolating the vesicles from the parent microbes. As described at 250, this may include the removal of bacterial toxins. The microbes and vesicles may be lyophilized, packaged in a powder or in solution, or prepared and packaged in any other suitable fashion. Continuing at 280, the packaged microbes and vesicles may be administered to a patient, as described for vesicles at 260.

Additionally or alternatively, the parent microbes themselves may be harvested and packaged directly, rather than harvesting vesicles separate from the parent microbes. Initial agent molecules may be applied to microbes for uptake as described with regard to 220 of FIG. 2. In some examples, the parent microbes may then be harvested and prepared for packaging without vesicle production being stimulated.

As an example, a pink children's ibuprofen suspension was added to a sufficient amount of fresh yogurt that can fully in vitro extracellularly vesiculate (IVEV) all the ibuprofen molecules along with live dry probiotic powder, then stirred to make the whole medium thoroughly blended. The mixture was incubated at room temperature for a period of time (depending on the amount of ibuprofen added) to form the fully IVEVed ibuprofen, then prepared for viewing under the microscope.

Figure 3:
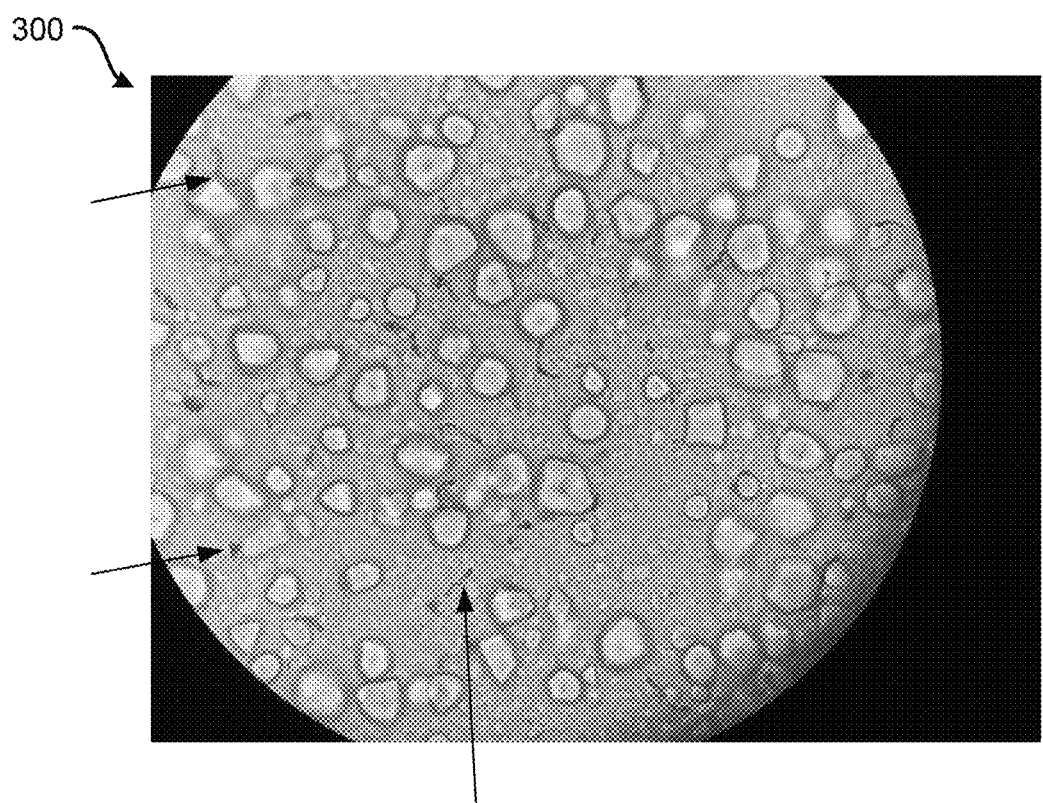
FIG. 3 shows a photograph of a probiotic culture following application of a dyed mixture of exogenous molecules.

FIG. 3 shows a photographic image 300 taken using a 1000× light microscope. As depicted color only showed up inside the OMV/EVs (visible as pink chains connected to each other, identified by arrows). There is no color visible outside the OMVs/EVs, indicating that all the dye molecules were E-vesiculated by the OMVs/EVs. As all the pink dye molecules are inside the OMVs/EVs, it can be logically inferred that all the Ibuprofen molecules should also be inside the OMVs/EVs, as it is unlikely that these natural probiotic cells could have the ability to select what molecules to be E-vesiculated and what not to be. From the perspective of the probiotic cells used in this experiment, the pink dye molecules and the Ibuprofen molecules are the same, as they both are exogenous. In other words, the probiotics non-specifically E-vesiculate xenobiotics within their growth media. Under the microscopy, the parent probiotics cells were observed as dead, surrounded by extracellular vesicles they produced, packed with IVEVed pink Ibuprofen molecules.

Accordingly, in vitro, bacteria are able to non-specifically E-vesiculate small molecules present in their extracellular environment. In vivo, bacteria should act the same way as they do in vitro to E-vesiculate whatever is present in their extracellular environment.

In another experiment, in vitro E-vesiculation of synthetic selenium molecules was performed using the same probiotics. Synthetic selenium was first resolved in water and added to a probiotic medium as described above. EVs of synthetic selenium molecules inside were formed, but under 1000× microscope, they appear as very tiny dots that are barely perceptible (Photos not shown). However, the whole medium changed color from crystal to red, which indicates that E-vesiculation did occur.

These experiments also indicate that OMVs/EVs' morphology is highly heterogeneous. The OMVs/EVs tend to carry a maximum load of exogenous cargo molecules, but not to the extent of being broken down along the transportation route.

Figure 4:
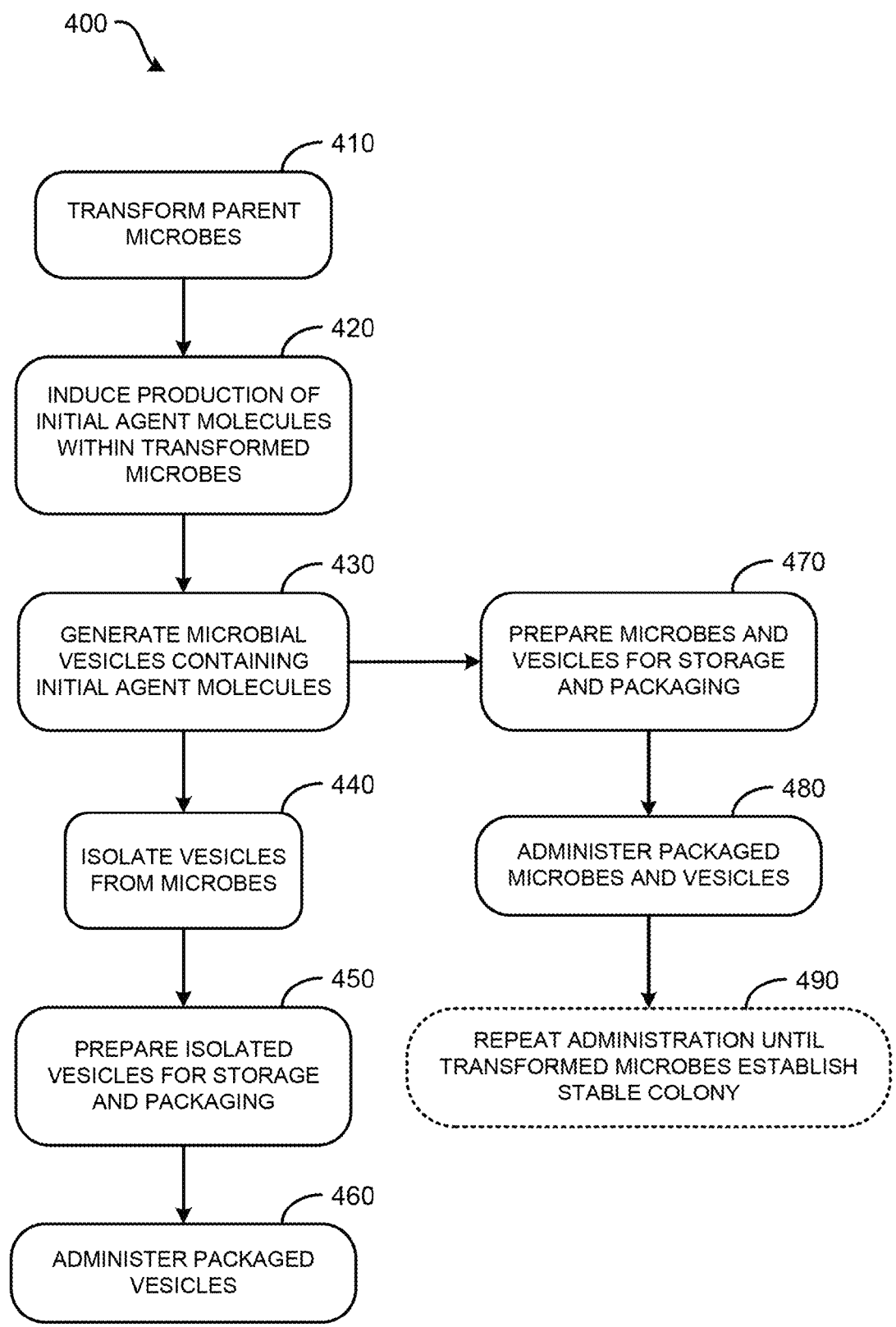
FIG. 4 depicts a flow-chart for a method of producing and administering agent molecules via microbial vesicles generated from engineered microbes.

FIG. 4 shows a flow chart for an additional example method 400 for producing and administering agent molecules via microbial vesicles. In this example, microbes are engineered to produce the initial agent molecules, rather than externally presenting the initial agent molecules to the microbes for uptake. Method 400 may be applied as a whole or in part to produce and/or administer agent molecules to a host organism via microbial vesicles. Method 400 may be applied to all marketed drugs, both currently available or later developed, including biologics, for human and animals that are capable of being synthesized in vivo.

At 410, method 400 includes transforming the parent microbes. As described with regard to FIG. 2, the parent microbes may be probiotic microbes and/or non-probiotic microbes, such as gram-negative bacteria, gram-positive bacteria, yeast, etc. Transforming the parent microbes may include providing the microbes with one or more plasmids encoding one or more expressible genes. For example, the parent microbes may be provided with plasmids for genes encoding enzymes for producing one or more initial agent molecules.

In some examples, multiple genes may be expressed to generate a single initial agent molecule. Such genes may be encoded on a single plasmid, or across multiple plasmids. Each gene product may operate independently, and/or may operate on a molecular product generated by another gene product as part of a sequential synthesis reaction. In some examples, an initial (starting point) precursor molecule may be an essential molecule (e.g., amino acid) that is present within the growth media for the microbes. In some examples, other, naturally occurring gene products may generate an initial precursor molecule from essential molecules. In other examples, an initial precursor molecule may be added to the growth medium. When multiple genes are expressed, they may originate from a single species (e.g., the natural producer of the initial agent molecule), or from multiple species.

In some examples, the genes may be configured to be expressed constitutively. In other examples, expression of the genes may be selectively inducible. In such examples, wherein multiple genes are transformed into the microbes, expression of the genes may be controlled by a common promoter, or each gene may be controlled by a unique promoter. As described with regard to FIG. 2, the microbes may be transformed to express proteins, either selectively or constitutively, that traffic to microbial vesicles upon vesicle generation.

At 420, method 400 includes inducing production of initial agent molecules within the transformed microbes. In some examples, the transfected genes may be expressed constitutively during typical microbial growth conditions. Inducing production may include stimulating transcription of one or more genes inserted into the microbes. For example, each plasmid may comprise a promoter region that enables transcription in the presence of one or more molecules (e.g., IPTG, lactose, arabinose). In some examples, production may be repressed in the presence of one or more molecules (e.g., glucose), the repression lifted upon metabolism of the repressor molecule(s). In examples wherein the microbes are transformed with two or more gene constructs, the genes may have a common promoter, and thus be responsive to the same induction conditions, or may have different promoters. As such, inducing production of initial agent molecules may include adding one or more molecules to the microbial growth media to induce transcription of the genes inserted into the microbes.

Inducing production of initial agent molecules within the transformed microbes may further include adding one or more agent precursors to the growth medium. Agent precursors may be added prior to, concurrent with, or following the addition of any transcription inducing agents. Agent precursors may be derived via natural extraction, synthesis, and/or semi-synthesis. For agent precursors derived from natural extraction methods, one or more components of the natural production source may be added to the uptake medium (e.g., cold-pressed juices of the natural production source).

Continuing at 430, method 400 includes generating microbial vesicles containing the initial agent molecules. As described with regard to 230 of FIG. 2, generating microbial vesicles may include providing the microbes with one or more additional factors and/or molecules, generating stress conditions, etc. Further, expression of additional proteins targeted to the vesicles may be induced. In some examples, the transformed parent microbes may be induced to produce the initial agent molecules. The initial agent molecules may then be isolated and applied to the transformed parent microbes for uptake and/or E-vesiculation.

At 440, method 400 includes isolating vesicles from microbes. As described with regard to 240 of FIG. 2, isolating vesicles may include breaking down outer cell walls and/or membranes, separating the vesicles from large aggregates and intact microbes, and concentrating and/or precipitating the isolated vesicles.

At 450, method 400 includes preparing isolated vesicles for storage and packaging. As described with regard to 250 of FIG. 2, preparing isolated vesicles for storage and packaging may include removing toxins from the vesicles, lyophilizing the vesicles, combining the lyophilized vesicles with one or more additional components, rehydrating the vesicles to form a suspension, and/or encapsulating the vesicles. At 460, method 400 includes administering packaged vesicles. Based on the packaging performed at 450, the packaged vesicles may be administered to a patient in any suitable manner.

Alternatively, method 400 may proceed from 430 to 470. At 470, method 400 includes preparing microbes and vesicles for co-storage and co-packaging. In other words, microbial vesicles may be generated following application of the initial agent molecules, and then the microbes may be harvested and prepared for packaging without isolating the vesicles from the parent microbes. As described at 450, this may include the removal of bacterial toxins. The microbes and vesicles may be lyophilized, packaged in a powder or in solution, or prepared and packaged in any other suitable fashion. Continuing at 480, the packaged microbes and vesicles may be administered to a patient, as described for vesicles at 460.

Additionally or alternatively, it may be desired to establish a stable colony of the transformed microbes in the host. As such, optionally, at 490, method 400 may include repeating the administration of packaged, transformed microbes and vesicles (480) until the transformed microbes establish a stable colony in the host. In some examples, new batches of microbes and vesicles containing the initial agent molecules may be generated, packages, and administered. With a stable colony established, vesicles containing the initial agent molecules may be generated constitutively, responsive to conditions within the host, and/or responsive to administration of one more exogenous molecules.

As an example, 100% pure vitamin B, whether extracted from natural products or synthetic is red, not water-soluble like red paint. While in the nature, vitamin B never exists in its isolated form, it's always inside the IVs of the eukaryotic cells that produce it. Since it's a holistic part of a whole IV with proteins on the IV's membrane, the color of natural vitamin B is always orange instead of red.

Figure 5:
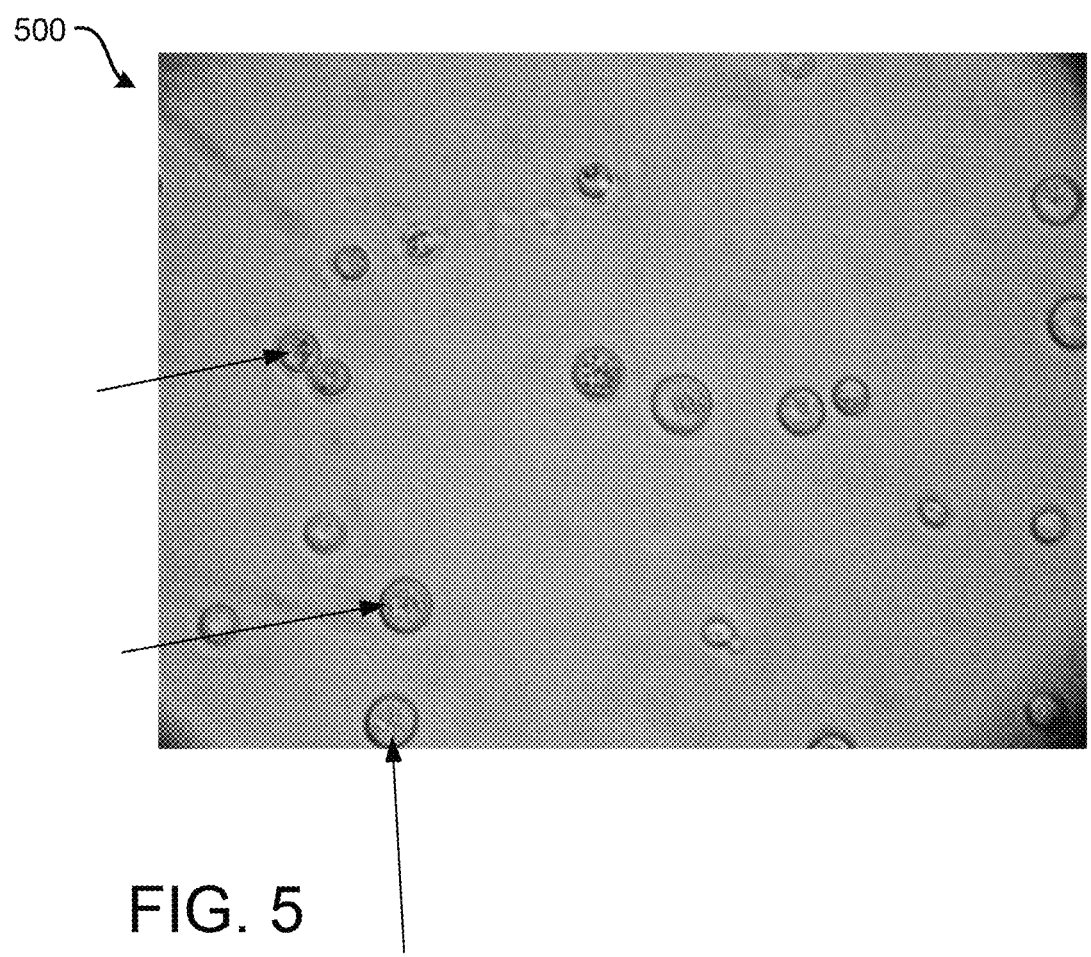
FIG. 5 shows a photograph of recombinant yeast cells transformed to produce vitamin B.

As an example of color difference between synthetic and natural vitamin, FIG. 5 shows a photograph of recombinant yeast cells transformed to produce vitamin B. As shown, vesicles with natural carotenoids are the color orange, and all the orange color visible in the yeast is inside the vesicles. This indicates that molecules produced in a eukaryotic cell are packaged in intracellular vesicles.

Figure 6:
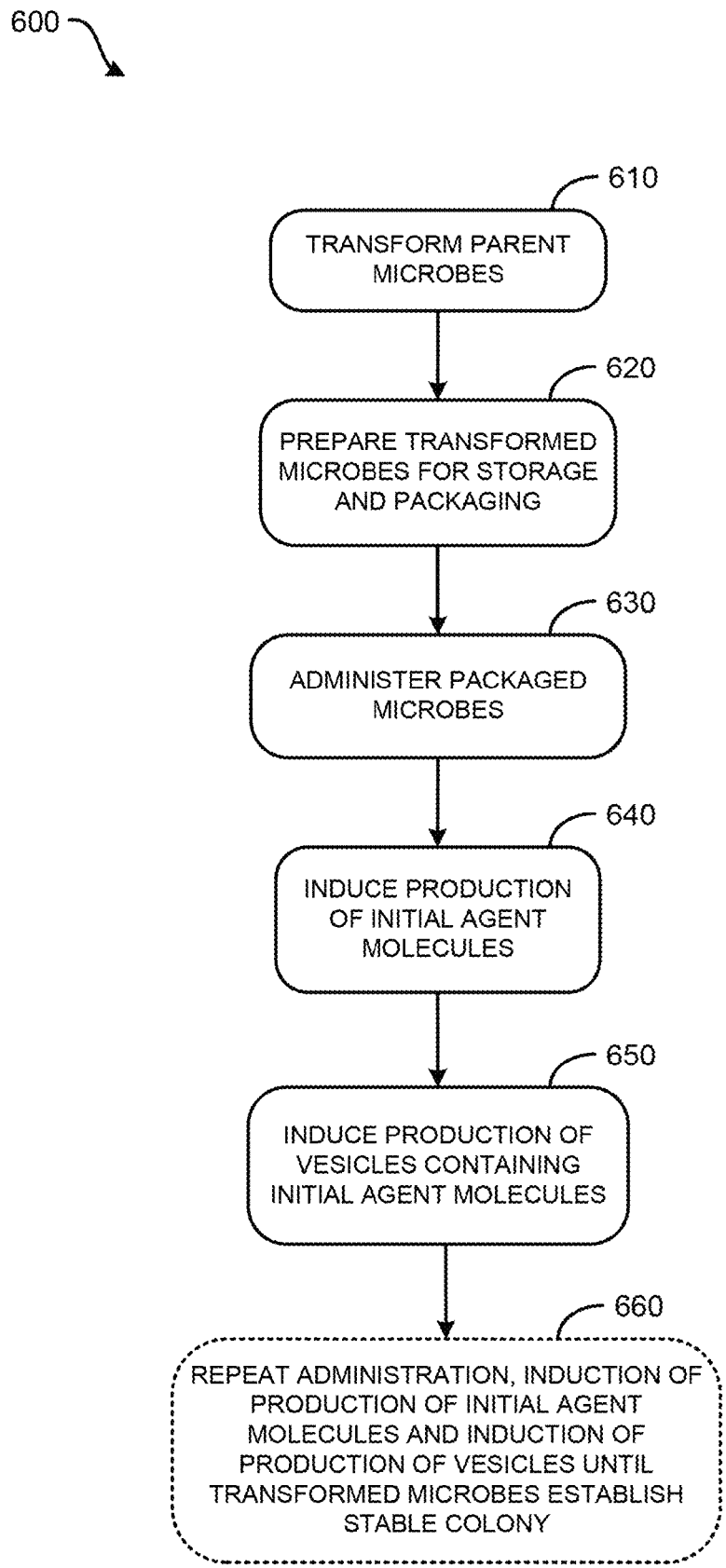
FIG. 6 depicts a flow-chart for a method of producing and administering agent molecules via genetically engineered probiotic microbes.

FIG. 6 shows a flow chart for an additional example method 600 for of producing and administering agent molecules via genetically engineered probiotic microbes. In this example, microbes are engineered to produce the initial agent molecules, and then used to seed a colony in a patient's gut. Method 600 may be applied as a whole or in part to prepare and/or administer agent molecules to a host organism via genetically engineered probiotic microbes. Method 600 may be applied to all marketed drugs, both currently available or later developed, including biologics, for human and animals that are capable of being synthesized in vivo.

At 610, method 600 includes transforming parent microbes. As described with regard to 410 of FIG. 4, transforming the parent microbes may include providing the parent microbes with one or more genes expressing enzymes used in the generation of one or more agent molecules. Transforming the parent microbes may further include providing the parent microbes with one more genes encoding proteins involved in vesicle formation, one more genes encoding proteins configured to traffic to vesicles, etc.

The promoters for the transformed genes may provide constitutive expression, and/or may be configured to respond to conditions within the human gut. For example, the promotors may be responsive to stress-related factors, infection and/or other disease related factors, nutrient deficiencies, gut pH, etc. As such, initial agent production and/or vesicle production may be enhanced by a threshold presence of one or more factors within the gut. In some examples, initial agent production and/or vesicle production may be induced by way of one or more factors that can be ingested by the patient (e.g., a food or beverage that includes the inducing factor).

In some examples, the transformed parent microbes may be induced to produce the initial agent molecules. The initial agent molecules may then be isolated and applied to the transformed parent microbes for uptake and/or E-vesiculation.

At 620, method 600 includes preparing the transformed microbes for storage and packaging. As described with regards to FIGS. 2 and 4, the transformed microbes may be detoxified and lyophilized. The transformed microbes may then be combined with one or more additional factors and then packaged for administration. At 630, method 600 includes administering the packaged microbes. In order to seed a gut flora colony, the packaged microbes may be administered orally and/or rectally. For example, the microbes may be packaged into enteric capsules which may be taken orally.

At 640, method 600 includes inducing production of the initial agent molecules. In some examples, inducing production of the initial agent molecules may occur after a duration following administration, in order to allow a gut flora colony to be established. In some examples, the production of the initial agent molecules may be constitutive. As described with regard to 610, in other examples, the production of initial agent molecules may be induced by conditions and/or factors present in the patient's gut. In still other examples, the production of initial agent molecules may be externally induced, such as the patient ingesting an additional molecular factor.

At 650, method 600 includes inducing production of vesicles containing the initial agent molecules. As per inducing production of initial agent molecules, production of vesicles may be constitutive, internally regulated, or externally induced. Production of vesicles may be concurrent with the production of the initial agent molecules, or may occur subsequently. For example, an internal factor may induce production of the initial agent molecules. Buildup of the initial agent molecules may then induce production of vesicles. As another example, the patient may ingest a first induction factor to induce production of the initial agent molecules. After a pre-determined duration, the patient may ingest a second induction factor to induce production of vesicles containing the initial agent molecules.

Additionally or alternatively, it may be desired to establish a stable colony of the transformed microbes in the host. As such, optionally, at 660, method 600 may include repeating the administration of packaged, transformed microbes (630), induction of production of initial agent molecules (640), and induction of production of vesicles (650), until the transformed microbes establish a stable colony in the host. With a stable colony established, vesicles containing the initial agent molecules may be generated constitutively, responsive to conditions within the host, and/or responsive to administration of one more exogenous molecules.

As an example, bitter melon has gained popularity as a natural treatment for diabetes. The inventor herein believes that bitter melon doesn't modulate insulin production or act upon any hormones as conventionally presumed, as bitter melon lowers glucose immediately after being taken, and doesn't interfere with hormone production. Rather, the inventor believes that when bitter melon is ingested, the momordicin stresses the resident bacteria, which in turn have to absorb more glucose to neutralize the momordicin (bitterness being the exact opposite of sweetness). Thus, the glucose in the blood system becomes reduced, but this effect is temporary.

As such, an example application of method 600 includes using transformed prokaryotes which upregulate production of momordicin in response to increased glucose. Genes involved in the production of momordicin and/or other anti-diabetic agents (e.g., charantin, vicine, polypeptide-p) and/or their derivatives may be isolated from bitter melon DNA and transformed into microbes, such as probiotics and/or the resident prokaryotes of the bitter melon or growing soil which directly influence the production of the anti-diabetic agents. The microbes may be extracted from the soil of bitter melon plants which have a high bitterness and/or high natural momordicin production. In some examples, the transformed genes may be placed under control of a glucose-sensitive promoter. The transformed microbes may be packaged and administered as described at 620 and 630, respectively. Production of momordicin may be induced by glucose concentrations above a threshold, such as levels considered to be unhealthy to the patient. Production of vesicles containing momordicin may be induced as described at 650. If necessary, the transformed microbes may be re-administered until a stable colony is established in the host.

Additionally or alternatively, if particular gut microbes can be identified as being associated with a particular disease, those particular gut microbes may be isolated from a patient. The isolated microbes may then be transformed and replaced in the patient's gut, thereby enabling an individualized drug by inducing the patient's own re-engineered gut microbes to generate the desired drug.

Figure 7:
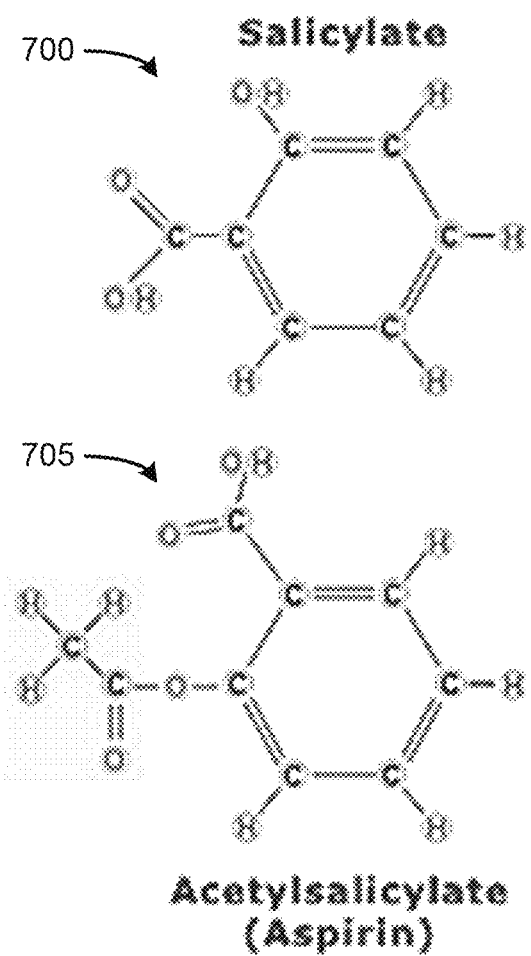
FIG. 7 schematically illustrates the molecular structures of aspirin and salicylate.

As an example, FIG. 7 depicts the molecular structure of salicylate (700) and aspirin (705). Willow bark comprises a molecule called salicin, which is converted in the body to an acidic derivative called salicylate. Aspirin, or acetylsalicylate is generated by adding an acetyl group to salicylate, thus making the molecule less acidic and easier to digest without significantly reducing the molecule's effectiveness at inducing pain relief.

Thus, in one example, microbes may be grown on media that includes willow bark extract, and thus includes the initial agent molecule of salicin. The microbes may be engineered to express enzymes that process salicin into salicylate and/or acetylsalicylate, that stabilize any of the salicin derivatives, and/or that aid in diverting salicin and/or its derivatives into microbial vesicles. In other examples, microbes may be grown on media that includes willow bark extract and further includes synthetic salicin, salicylate, and/or acetylsalicylate. Additionally or alternatively, the microbes may be transformed with genes expressed in willow in the generation of salicin. The microbes may be grown in growth media that includes one or more salicin precursors and/or willow bark extracts.

Upon uptake and/or production of salicin or its derivatives, production of microbial vesicles may be induced, as described with regard to FIGS. 2 and 4. As described with regard to FIG. 6, in some examples, the microbes may be administered directly with the goal of establishing a gut colony of microbes engineered to produce salicin or its derivatives.

Figure 8:
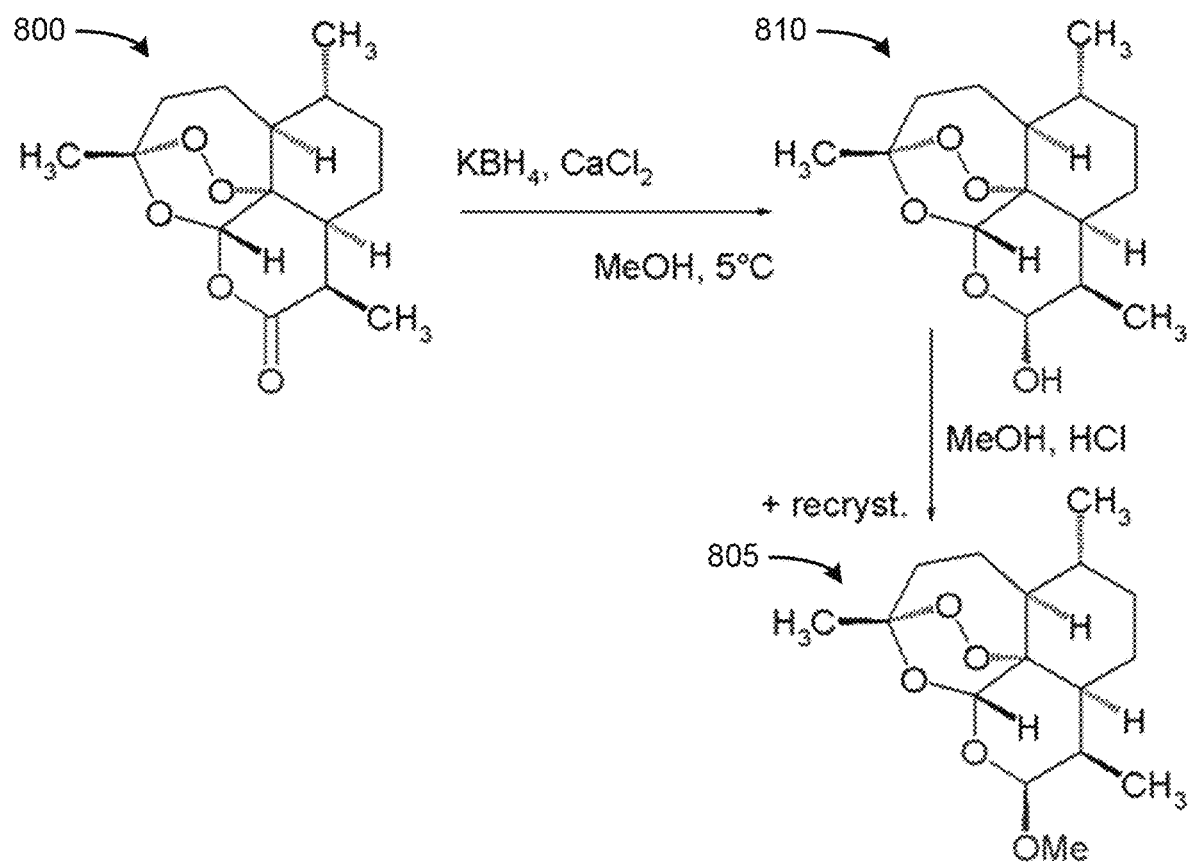
FIG. 8 schematically illustrates the molecular structures of artemether and its precursors.

As another example, FIG. 8 depicts the molecular structure of artemisinin (800) and artemether (805). Artemether is an anti-malarial drug that is semi-synthesized from plant *Artemisia annua*. Naturally occurring artemisinin is extracted, an undesirable lactone ring in artemisinin is then replaced by an acetal by reduction with potassium borohydride, followed by methoxylation to form artemether.

Thus, in one example, microbes may be grown on media that includes extracted artemisinin. The extracted artemisinin may be less than 100% pure (e.g., contains other derivatives of *Artemesia annua*. Different purity levels may be applied to determine the most effective means of uptake and/or efficacy when administered.

In another example, the microbes may be transformed with genes expressed in *Artemisia annua* in the generation of artemisinin. The microbes may be grown in growth media that includes one or more artemisinin precursors and/or artemisia extracts.

Upon uptake and/or production of artemisinin or its derivatives, production of microbial vesicles may be induced, as described with regard to FIGS. 2 and 4. As described with regard to FIG. 6, in some examples, the microbes may be administered directly with the goal of establishing a gut colony of microbes engineered to produce artemisinin or its derivatives.

Other examples of plant-based agent molecules include Taxol, derived from Pacific Yew and used to treat breast cancer, and Metformin, derived from *Galego officinalis* and used to treat type 2 diabetes. Extracts from bitter melon may also be used in diabetes treatments.

Other agent molecules such as avermectins and penicilin can be generated as fermentation products but are purified (or synthesized) for administration. Harvesting these agent molecules within microbial vesicles may increase their efficacy.

A potential advantage of using E-vesiculation methods is a reduced occurrence of side effects, such as diarrhea. The phenomena that diarrhea is the most common side effect of any medication supports the concept that chemically exogenous molecules inhibit resident prokaryotes. Diarrhea indicates microbiota dysbiosis, chemical exogenous molecules change microbiota composition and break the homeostasis prior to the killing thus cause diarrhea. E-vesiculated agent molecules may reduce the occurrence of diarrhea, as the agent molecules are first packaged in vitro prior to administration leaving no room for any resident or nonresident bacterial pathogens to hijack them before they reach the destination host cells.

Another potential advantage of using E-vesiculation methods is a reduced occurrence of drug resistance. Host eukaryotic cells, even cancer cells, the most aggressive cells, are demonstrated not able to E-vesiculate xenobiotics like its resident bacteria do. Rather, they rely on resident bacteria to E-vesiculate and transport exogenous molecules to them for uptake. Drug resistance may occur when exogenous drug molecules are hijacked by "bad" resident bacteria who E-vesiculate/denature drug molecules into their MDEVs, allowing those E-vesiculated drug molecules to be absorbed by cancer cells as nutrients. Packaging drug molecules into MDEVs derived from favorable, "good" probiotics may allow them to escape these metabolic pathways and thus prevent the development of drug resistance.

Inventor has conducted preliminary experiments demonstrating the efficacy of E-vesiculated drugs. In one example, diabetes and hypertension drug doses were cut in half but normal blood glucose and blood pressure were maintained. In another example, the inventor observed that E-vesiculated metformin HCl was sufficient to reduce blood glucose immediately, without side effects such as diarrhea. In yet another example, the inventor observed that E-vesiculated Levofloxacin was sufficient to reverse chronic drug resistance.

Plants may also benefit from the E-vesiculation of fertilizers and/or pesticides. Plant fertilizers are generally classified as organic or inorganic. Organic fertilizers are beneficial to the environment, but often need to be broken down by resident plant or soil microbes and are thus slow acting. Inorganic fertilizers are generally fast acting but are lost from the soil quickly and thus require application in high concentrations which can damage the local environment. Modifying the plant genome to produce pesticides or growth agents may have unintended consequences, both for the plant itself and the local environment. Alternatively, E-vesiculated fertilizers, pesticides, and growth factors may be applied to, or produced by, endophytic microbes, and then directed to vesicles which may then be provided to plants. The vesicles may provide rapid, directed uptake, thereby reducing the amount of material applied as well as reducing the amount of excess material escaping into the external biome.

Figure 9:
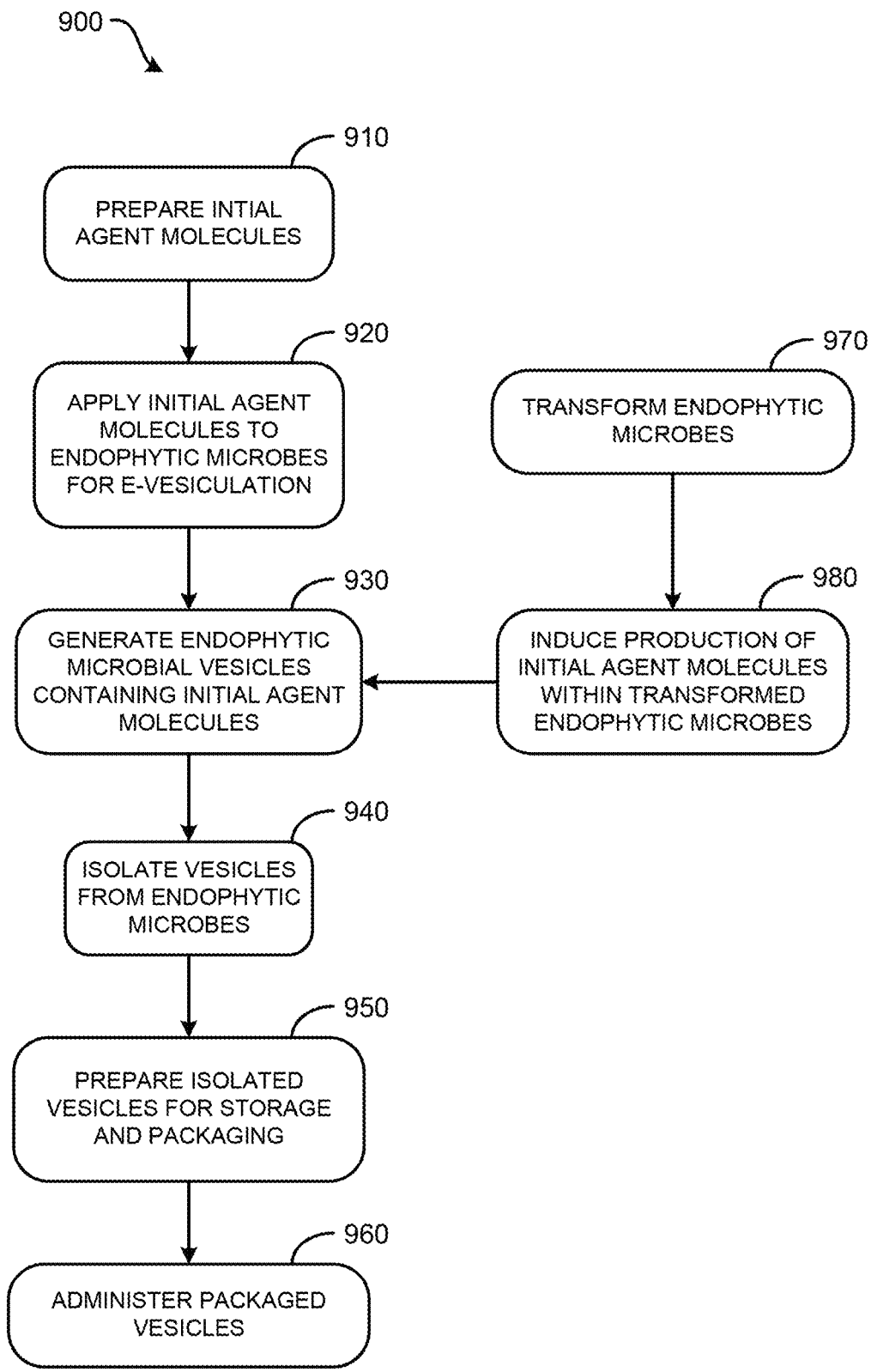
FIG. 9 depicts a flow-chart for a method of preparing and administering agent molecules via endophytic microbial vesicles.

FIG. 9 depicts a flow chart for a method 900 for preparing and administering agent molecules via endophytic microbial vesicles. Method 900 may be applied as a whole or in part to prepare and/or administer agent molecules to a host organism via endophytic microbial vesicles. Method 900 may be applied to all marketed fertilizers and biocides for plants, both currently available or later developed. At 910, method 900 includes preparing initial agent molecules. Initial agent molecules may include synthesized and/or natural fertilizers (e.g., Ammonium Nitrate, Ammonium Phosphate, Superphosphate, Potassium Sulfate, monoammonium phosphate, diammonium phosphate), synthesized and/or natural pesticides (e.g., Imidacloprid (Nicotine), plant antibiotics), synthesized and/or natural plant growth factors (e.g., Auxin, Cytokines), phytohormones (e.g., indole-3-acetic acid, steroids, terpenoids, diterpenes), binding agents for nitrogen, phosphorous, iron, ethylene, etc. Initial agent molecules may be prepared via extraction or partial extraction from a natural production source, via synthesis, via semi-synthesis, etc. In some examples, the initial agent molecules may include precursors for an active form of the agent molecules. The initial agent molecules may undergo enzymatic modification and/or metabolism to generate the active agent molecules.

At 920, method 900 includes applying the initial agent molecules to endophytic microbes for uptake and/or E-vesiculation. Microbes may include endophytic bacteria (e.g., *Pseudomonas, Streptomyces, Acidovorax facilis, Bradyrhizobium, Rhizobium, Rhodococcus rhodochrous*), endophytic fungi (e.g., *Colletotrichum, Curvularia, Epichloe, Fusarium, Mycosphaerella, Neotyphodium, Piriformospora, Serendiptia*), endophytic algae (e.g., *Pythium oligandrum*) or other single celled microorganisms. In some cases, pathogenic bacteria which have been identified as being capable of coopting a plant's membrane fusion process may be genetically engineered to be less pathogenic. Endophytic microbes may be selected arbitrarily or based on the target host. In some examples, endophytic microbes may be harvested from the target host, target soil, etc. and then expanded in culture. In some examples, multiple cultures of endophytic microbes may be selected for one target host. For example, specific mycorrhizal symbionts from a plant's rhizosphere may be selected, as well as specific microbes from one or more domains of a plant's phylloshpere. These cultures may be treated with the same agent molecules or different agent molecules.

Endophytic microbes may be grown in any suitable culture medium. Initial agent molecules may be applied to the endophytic microbes for uptake and/or E-vesiculation in the original growth medium, or in a medium specific for promoting E-vesiculation. For example, the initial agent molecules may be applied in a growth medium that includes additional amino acids, peptides, sugars, etc. For initial agent molecules extracted from a natural production source, one or more components of the natural production source may be added to the growth medium. For example, the growth medium may be enriched with cold-pressed juices of the natural production source. In some examples, one or more reagents may be added to promote microbial tolerance of the initial agent molecules, to promote microbial uptake of the initial agent molecules, and/or to stabilize the initial agent molecules in the growth medium and/or within the microbes and/or vesicles following application.

Application may proceed for a predetermined duration and/or based on culture conditions. In some examples, the initial agent molecules may be replenished one or more times following the initial application. Uptake may be determined by assaying the media for depletion of the initial agent molecules, by assaying the microbes themselves (e.g., via spectrometry for color or fluorescence changes associated with uptake), or by any other suitable means.

At 930, method 900 includes generating endophytic microbial vesicles that contain the initial agent molecules. Upon application of the initial agent molecules, some endophytic microbes may generate vesicles that contain the initial agent molecules without additional stimulation. In some examples, one or more additional factors and/or molecules may be provided to the microbes in order to further stimulate vesicle formation.

Generating endophytic microbial vesicles may further include expressing and targeting proteins to the vesicles. For example, the endophytic microbes may be transformed to express proteins, either selectively or constitutively, that traffic to the vesicles upon vesicle generation. The endophytic microbes may be transformed with expression constructs that are inducible, responsive to one or more exogenously added molecules and/or to one or more endogenously generated proteins.

At 940, method 900 includes isolating vesicles from endophytic microbes. Following the generation of endophytic microbial vesicles loaded with initial agent molecules, the vesicles may be isolated from the endophytic microbes. However, depending on the microbes used, the vesicles may not be separated from the parent microbes. For eukaryotic microbes, such as yeast, the cell walls may first be broken down, as the vesicles are internally located.

At 950, method 900 includes preparing the isolated vesicles for storage and packaging. In particular, toxins may be removed from membranes prior to packaging the vesicles for administration. In some examples, this may be accomplished by pretreatment of the parent bacteria or isolated vesicles with detergents. Isolated vesicles may be lyophilized (i.e., freeze-dried) and packaged for administration.

In some examples, the isolated vesicles may be packaged in a powder (i.e., dry) form. The lyophilized vesicles may be combined with one more additional dry components, for example, one or more additional sugars, proteins, small molecules, etc. In some examples, the lyophilized vesicles may be resuspended in solution (e.g., aqueous solution), and may be co-suspended along with one or more additional components. Dry compositions and suspensions may be further packaged, for example by pelletization.

At 960, method 900 includes administering the packaged vesicles to a plant. Depending on the packaging described at 950, the isolated vesicles may be administered to a user in numerous manners. The type of packaging and administration may be determined based on dosage, the target regions, etc. For example, the isolated vesicles may be administered as a dry powder, as a suspension, in pelletized form, etc. Further, suspensions of isolated vesicles may be aerosolized.

Additionally or alternatively, vesicles may be isolated from parent endophytic microbes prior to the application and uptake of the initial agent molecules. Microbial vesicles may be generated and isolated from parent microbes as described with regard to 930 and 940 of FIG. 9. The isolated microbial vesicles may then be loaded with the initial agent molecules by any suitable means, such as via electroporation. When the vesicle membranes have stabilized after a duration following electroporation, the loaded vesicles may be prepared for packaging, as described with regard to 950 of FIG. 9.

Alternatively, method 900 may begin at 970. At 970, method 900 includes transforming the endophytic microbes. Transforming the parent microbes may include providing the microbes with one or more plasmids encoding one or more expressible genes. For example, the parent microbes may be provided with plasmids for genes encoding enzymes for producing one or more initial agent molecules. In some examples, the genes may be configured to be expressed constitutively. In other examples, expression of the genes may be selectively inducible. In such examples, wherein multiple genes are transformed into the microbes, expression of the genes may be controlled by a common promoter, or each gene may be controlled by a unique promoter. As described with regard to FIG. 2, the microbes may be transformed to express proteins, either selectively or constitutively, that traffic to microbial vesicles upon vesicle generation.

At 980, method 900 includes inducing production of initial agent molecules within the transformed endophytic microbes. In some examples, the transfected genes may be expressed constitutively during typical microbial growth conditions. Inducing production may include stimulating transcription of one or more genes inserted into the microbes. Inducing production of initial agent molecules within the transformed microbes may further include adding one or more agent precursors to the growth medium. Following the induction of production of initial agent molecules within the transformed endophytic microbes, method 900 proceeds to 930, whereupon endophytic microbial vesicles that contain the initial agent molecules are generated.

In some examples, the vesicles may be co-packaged and/or co-administered with the parent microbes and/or transformed microbes. The transformed microbes may be configured to inducibly generate vesicles containing the initial agent molecules. The transformed microbes may be applied and re-applied to the host plants and/or soil until stable colonies are generated. Once stable colonies are in place, one or more factors may be applied to induce production of the initial agent molecules and/or one or more factors may be applied to induce production of vesicles containing the initial agent molecules.

According to an example of the present disclosure, a method comprises: preparing initial agent molecules; applying the initial agent molecules to microbes for extracellular vesiculation; generating microbial vesicles containing the initial agent molecules by the microbes; preparing the microbial vesicles for storage and packaging; and administering the packaged microbial vesicles to a host organism. In this example or any other example disclosed herein, the microbes are prokaryotes. However, it will be appreciated that in this example or any other example disclosed herein, non-prokaryote microbes (e.g., eukaryotes) may be used, and extracellular vesiculation may be replaced with or at least partially augmented by uptake and vesiculation of the initial agent molecules by the non-prokaryote microbes. In this example or any other example disclosed herein preparing the microbial vesicles for storage and packaging further comprises: isolating the microbial vesicles containing the initial agent molecules from the microbes to obtain isolated microbial vesicles; and preparing the isolated microbial vesicles for storage and packaging. In this example or any other example disclosed herein, preparing the microbial vesicles for storage and packaging further comprises: preparing the microbial vesicles and the microbes for storage and co-packaging, and wherein administering the packaged microbial vesicles further includes co-administering the co-packaged microbial vesicles and microbes to the host organism. In this example or any other example disclosed herein, preparing the initial agent molecules includes extracting the initial agent molecules from a natural production source. In this example or any other example disclosed herein, applying the initial agent molecules to the microbes for extracellular vesiculation further comprises applying the initial agent molecules to the microbes in the presence of cold-pressed juices of the natural production source. In this example or any other example disclosed herein, generating the microbial vesicles containing the initial agent molecules includes applying one or more factors that upregulate vesicle formation.

According to another example of the present disclosure, a method comprises: transforming parent microbes to obtain transformed microbes; inducing production of initial agent molecules within the transformed microbes; generating microbial vesicles containing the initial agent molecules by the transformed microbes; preparing the microbial vesicles for storage and packaging; and administering the packaged microbial vesicles to a host organism. In this example or any other example disclosed herein, preparing the microbial vesicles for storage and packaging further comprises: isolating the microbial vesicles containing the initial agent molecules from the transformed microbes; and preparing the isolated microbial vesicles for storage and packaging. In this example or any other example disclosed herein, preparing the microbial vesicles for storage and packaging further comprises: preparing the microbial vesicles and the transformed microbes for storage and co-packaging, and wherein administering the packaged microbial vesicles further includes co-administering the co-packaged microbial vesicles and the transformed microbes to the host organism. In this example or any other example disclosed herein, the method further comprises repeating administration of the co-packaged microbial vesicles and the transformed microbes until a stable colony is established in the host organism. In this example or any other example disclosed herein, the method further comprises initiating autoproduction of microbial vesicles containing initial agent molecules within the stable colony. In this example or any other example disclosed herein, transforming the parent microbes includes transforming the parent microbes with one or more inducible genes for one or more gene products involved in synthesizing the initial agent molecules in vivo.

According to yet another example of the present disclosure, a method comprises: transforming parent microbes to obtain transformed microbes; preparing the transformed microbes for storage and packaging; administering the packaged transformed microbes to a host organism; inducing production of initial agent molecules by the transformed microbes in the host organism; and inducing production of vesicles containing the initial agent molecules by the transformed microbes in the host organism. In this example or any other example disclosed herein, the method further comprises repeating administration of the packaged transformed microbes until a stable colony is established in the host organism; and initiating autoproduction of microbial vesicles containing initial agent molecules within the stable colony. In this example or any other example disclosed herein, the parent microbes are prokaryotes. In this example or any other example disclosed herein, the parent microbes are selected on the basis of not being harmful to a host organism to which the packaged transformed microbes are administered. In this example or any other example disclosed herein, the parent microbe is *Streptomycis avermectis*, and wherein the initial agent molecules are avermectin. In this example or any other example disclosed herein, the initial agent molecules include one more of: momordicine, charantin, polypeptide-p, vicine, and/or other anti-diabetic agents derived from bitter melon. In this example or any other example disclosed herein, the parent microbes include one or more bitter melon resident prokaryotes.

According to yet another example of the present disclosure, a composition for treating a host organism comprises the packaged or unpackaged isolated microbial vesicles disclosed herein as well as the packaged or unpackaged microbial vesicles derived from transformed parent microbes, be they isolated, unpackaged, packaged, and/or co-packaged with their transformed parent microbes disclosed herein that are produced via any of the methods disclosed herein.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for therapeutic treatment of a subject for diabetes, the method comprising:

culturing probiotic bacteria that are probiotic to the subject;

preparing initial agent molecules, the initial agent molecules exogenous to both the probiotic bacteria and the subject, the initial agent molecules including one or more of: momordicine, charantin, polypeptide-p, vicine, and/or other anti-diabetic agent obtained from bitter melon;

applying the initial agent molecules to the probiotic bacteria for extracellular vesiculation;

generating extracellular membrane vesicles containing the initial agent molecules from the probiotic bacteria;

preparing the extracellular membrane vesicles containing the initial agent molecules for storage and packaging at least by isolating the extracellular membrane vesicles containing the initial agent molecules from the probiotic bacteria;

packaging the isolated extracellular membrane vesicles; and administering the packaged isolated extracellular membrane vesicles containing the initial agent molecules to the subject.

2. The method of claim 1, wherein the probiotic bacteria are prokaryotes.

3. The method of claim 1, wherein applying the initial agent molecules to the probiotic bacteria for extracellular vesiculation further comprises applying the initial agent molecules to the probiotic bacteria in the presence of cold-pressed juices of the natural production source.

4. The method of claim 1, wherein generating the extracellular member vesicles containing the initial agent molecules includes applying one or more factors that upregulate vesicle formation.

5. The method of claim 1, wherein the initial agent molecules are applied to the probiotic bacteria in minimal growth media.

6. The method of claim 5, wherein the minimal growth media includes amino acids, peptides, and sugars.

7. The method of claim 1, wherein the probiotic bacteria that are cultured are gram-positive bacteria that are probiotic to the subject.

\* \* \* \* \*